Figure 1:
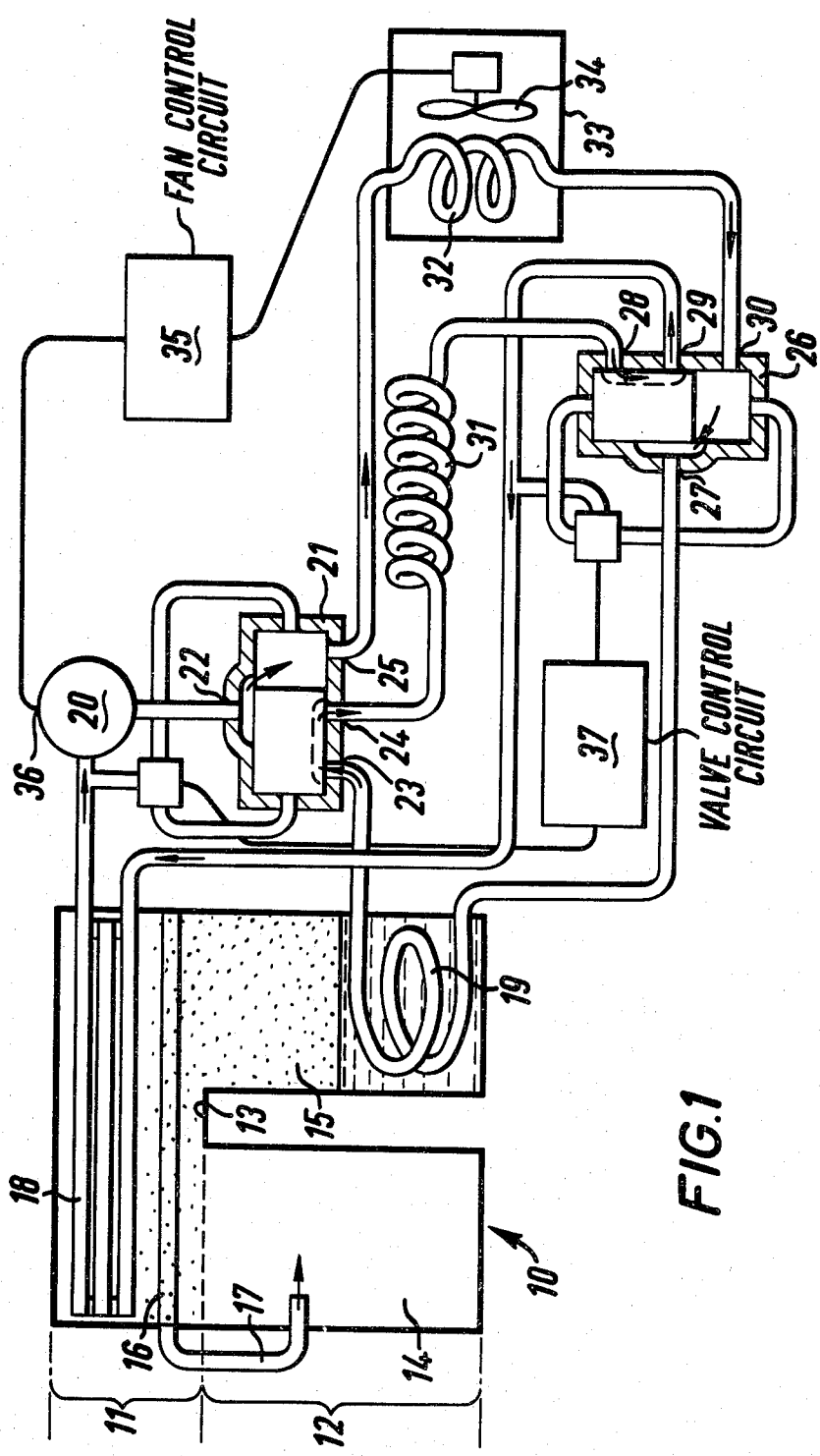

United States Patent [19]
Stevens et al.

[11] 4,278,502
[45] Jul. 14, 1981

[54] CHEMICAL RECOVERY APPARATUS

[76] Inventors: Christopher Stevens; John B. Stevens, both of Spirella Bldg., Cambridge Rd., Harlow, Essex, England

[21] Appl. No.: 97,652

[22] Filed: Nov. 27, 1979

Related U.S. Application Data

[63] Continuation of Ser. No. 911,041, May 30, 1978, abandoned.

[30] Foreign Application Priority Data

May 30, 1977 [GB] United Kingdom ............... 22827/77

[51] Int. Cl.$^3$ .......................... B01D 3/42; F25B 29/00
[52] U.S. Cl. .................................... 202/206; 202/235; 62/196 B; 203/2; 203/100; 203/DIG. 4
[58] Field of Search ..................... 203/24, 26, DIG. 4, 203/2, 100, DIG. 16, DIG. 18; 202/160, 206, 186, 235; 62/116, 238 E, 196 B

[56] References Cited

U.S. PATENT DOCUMENTS

| 1,466,670 | 9/1923 | Monti | 203/DIG. 4 |
|---|---|---|---|
| 2,933,904 | 4/1960 | Wellman | 62/305 |
| 3,029,614 | 4/1962 | Smith et al. | 62/324.6 |
| 3,134,241 | 5/1964 | Johnson | 62/196 B |
| 3,145,543 | 8/1964 | Miner | 62/149 |
| 3,308,877 | 3/1967 | Gerteis | 62/196 B |
| 3,389,576 | 6/1968 | Mauer | 62/196 B |
| 4,003,798 | 1/1977 | McCord | 203/DIG. 4 |
| 4,043,144 | 8/1977 | Klotz et al. | 62/196 B |
| 4,120,173 | 10/1978 | Kimpel | 62/196 B |

Primary Examiner—Wilbur L. Bascomb, Jr.
Attorney, Agent, or Firm—Stevens, Davis, Miller & Mosher

[57] ABSTRACT

Apparatus for purifying liquid including a container for the liquid, means for heating the liquid when in the container to vaporize the liquid, means for cooling the vapor to form a condensate and a collector for collecting the condensate, the heating means comprising a condenser of a refrigerant circulatory systems and the cooling means comprising an evaporator of the system so that refrigerant liquified in the condenser gives off heat to heat the said liquid and evaporation of the liquid in the evaporator causes heat to be absorbed from the vapor thereby cooling the vapor to for the condensate.

4 Claims, 3 Drawing Figures

CHEMICAL RECOVERY APPARATUS

This is a Continuation of application Ser. No. 911,041 filed May 30, 1978, and now abandoned.

This invention relates to chemical recovery apparatus.

It is well known to use evaporation and distillation techniques to obtain recovery of chemicals in chemical processes. There are, however, certain disadvantages in such techniques. One such disadvantage is that it is necessary to provide means for heating a liquid chemical to effect evaporation thereof and to provide additional means for cooling the vapour produced by the evaporation process to effect distillation of the vapour. Another disadvantage is that the evaporation process causes evaporation of other chemicals present in the chemical to be recovered and which other chemicals it is also desired to recover but which will be evaporated because they have a slightly higher boiling point compared with the boiling point of the principle chemical to be recovered. In consequence, the other chemicals are evaporated and may not necessarily be recovered during the distillation process.

According to the present invention there is provided apparatus for purifying liquid including a container for the liquid, means for heating the liquid when in the container to vapourise the liquid, means for cooling the vapour to form a condensate and a collector for collecting the condensate, the heating means comprising a condenser of a refrigerant circulatory system and the cooling means comprising an evaporator of the system so that refrigerent liquified in the condenser gives off heat to heat the said liquid and evaporation of the refrigerent in the evaporator causes heat to be absorbed from the vapour thereby cooling the vapourto form the condensate.

The apparatus may include first control means for directing flow of refrigerent in the system. The apparatus may include a second condenser. The first control means may be adapted to direct refrigerent sequentially through the second condenser and the said condenser during an operating period of the apparatus and sequentially through the said condenser and the second condenser during another operating period of the apparatus. The first control means may be adapted to direct refrigerent sequentially through the said condenser and an expansion device of the circulatory system during the said operating period and sequentially through the said condenser, the expansion device and the second condenser during the said another operating period of the apparatus. The first control means may be adapted to direct refrigerent sequentially through the said condenser, the second condenser and the expansion device during a further operating period of the apparatus. The first control means may comprise a plurality of slide valves.

The second condenser may be provided with cooling means. The cooling means may comprise a fan. The fan may be controlled by a second control means. The second control means may include a heat detecting device. The heat detecting device may be located in a compressor of the circulatory system.

Following is a description, by way of example only and with reference to the accompanying drawings, of one method of carrying the invention into effect.

Figure 2:
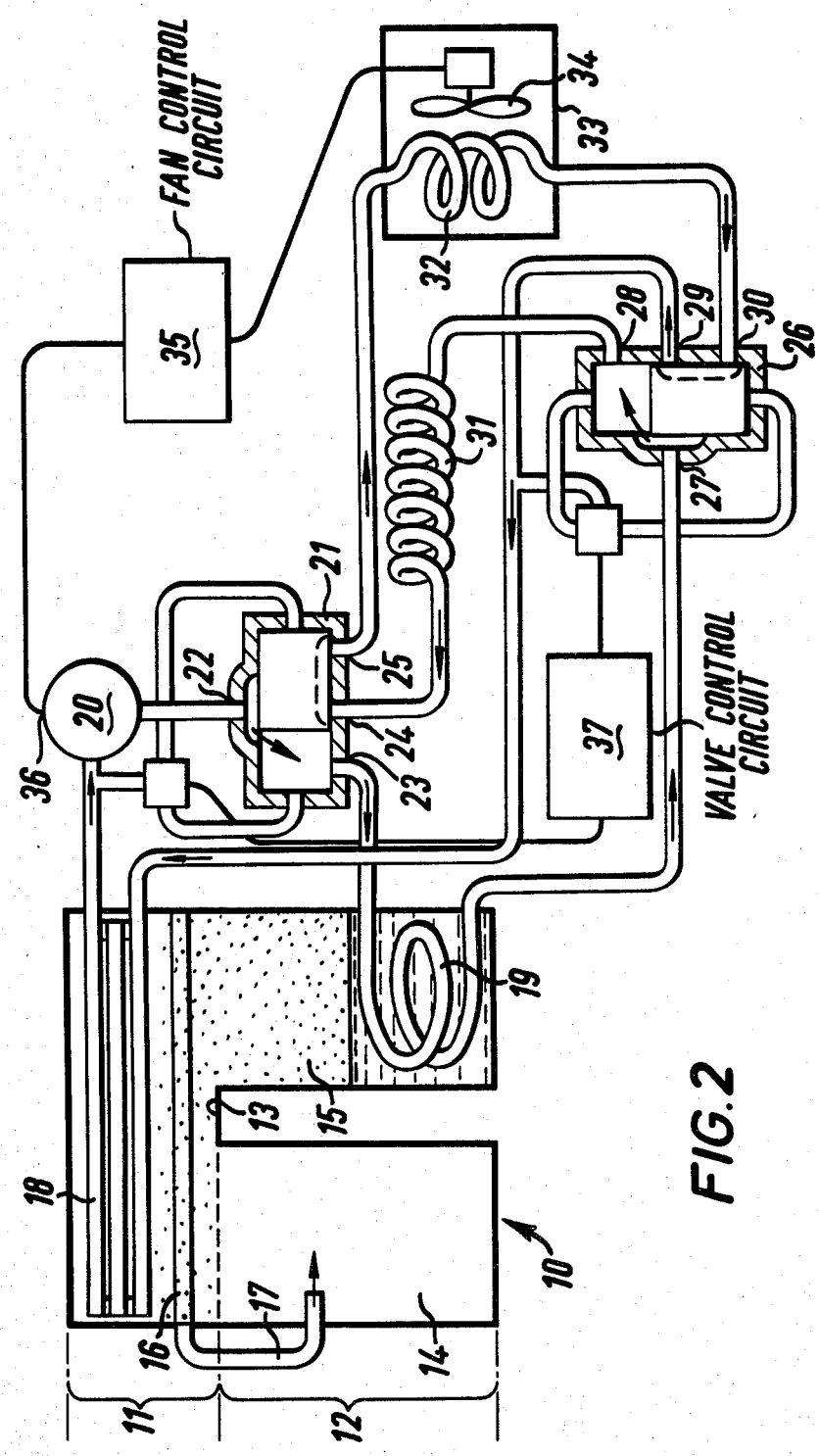
Figure 3:
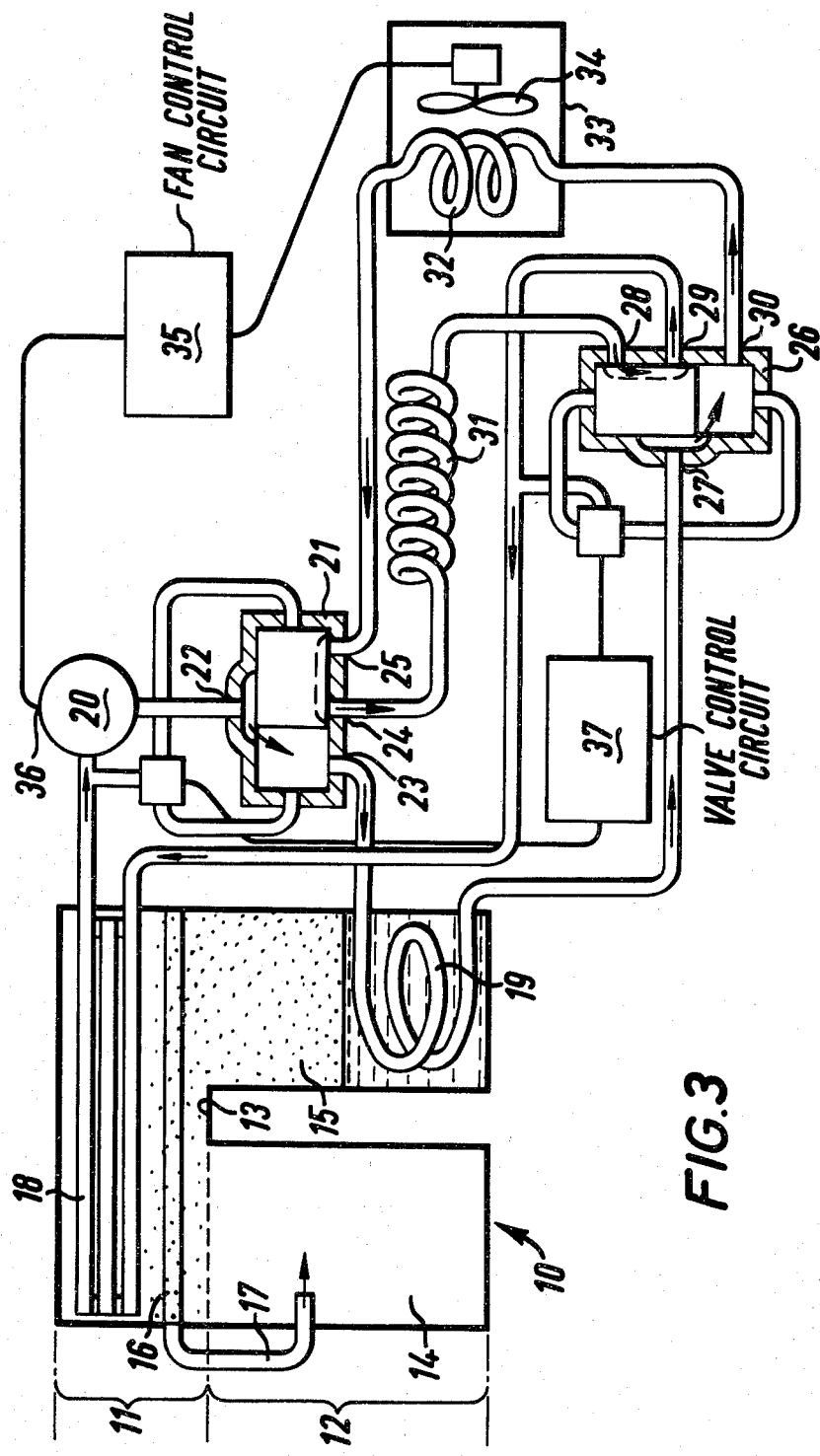

In the drawings:

FIG. 1 is a diagrammatic representation of apparats in accordance with the present invention, the apparatus being in a stand-by condition, FIG. 2 is a diagrammatic representation of the apparatus when in an initial warm up period, and FIG. 3 is a diagrammatic representation of the apparatus when in an operational condition.

Referring to FIG. 1 of the drawings, there is shown a tank 10 having an upper portion 11 and a lower portion 12. The lower portion 12 has two compartments 14, 15 separated by a weir 13.

The upper portion 11 of the tank 10 contains a drip tray 16 which extends above the compartments 14 and 15. One end of the tray 16 is connected to the compartment 14 by means of a conduit 17. The upper portion of the tank 10 also has located therein above the drip tray 16 an evaporator coil 18. The compartment 15 has located in the lower portion thereof a main condenser coil 19.

An outlet of the evaporator coil is connected to an inlet of a compressor 20. An outlet of the compressor 20 is connected to an inlet port 22 of a slide valve 21 having three outlet ports 23, 24 and 25. The outlet port 23 has connected thereto one end of the condenser coil 19 and the other end of the condenser coil 19 is connected to an inlet port 27 of a slide valve 26 having three outlet ports 28, 29 and 30. The outlet port 28 of the slide valve 26 is connected to the outlet port 24 of the slide valve 21 via a capillary coil 31. The outlet port 29 of the slide valve 26 is connected to the inlet of the evaporator coil 18. The outlet port of the slide valve 26 is connected to the outlet port 25 of the slide valve 21 via an auxiliary condenser coil 32. The auxiliary condenser coil 32 is contained within a housing 33 in which there is mounted an electrically operated fan 34.

The fan 34 is controlled by an electric circuit 35 which includes a thermistor 36 located in an upper portion of the compressor 20.

The slide valves 21 and 26 are controlled by an electrical control circuit 37.

The compartment 14 is provided with a tap (not shown) in a lower portion thereof for draining condensate collected in the compartment 14. The compartment 15 receives liquid to be purified. FIG. 1, the control circuit 37 controls the slide valves 21 and 26 so that refrigerent is circulated from the compressor 20, via the slide valve 21, the auxiliary condenser coil 32, the slide valve 26, the condenser coil 19, the capillary coil 31 and the evaporator coil 18.

When in the stand-by condition illustrated in FIG. 1 refrigerent is compressed by compressor 20 and directed via slide valve 21 to the aux condenser coil 32 where it gives up its heat of compression to its ambient surrounding (air, water, etc.) and condenses. The condensed liquid then passes via slide valve 26 to main condensor coil 19 where no change takes place as no temperature difference exists between condensor coil 19 and liquid in compartment 15. The liquid refrigerant is then directed via slide valve 21 to capillary coil 31 where it is expanded to a lower pressure and directed via slide valve 26 to the evaporator coil 18 where it absorbs heat from its ambient surroundings.

However, initially, it is necessary to rapidly heat the liquid in the compartment 15. This is achieved by operating the slide valves 21, 26 so that the refrigerent circulates as shown in FIG. 2 whereby the refrigerent is circulated from the compressor 20 via slide valve 21 to condensor coil 19 where it gives up its heat of compression and condenses. The liquid is directed via slide valve 26 to capillary coil 31, which expands the refrigerant to a lower pressure, and then to auxiliary condensor coil 32 where it absorbs heat from the coils ambient surroundings (air, water, etc.) it then passes to the evaporator coil where it absorbs further heat before returning to comp 20.

When the rate of vapourisation of the liquid in the compartment 15 is steady, the control circuit 37 operates the slide valves 21, 26 so that the refrigerent circulates from the compressor 20 through the condenser coil 19 via the slide valve 21, the auxiliary condenser coil 32 via the slide valve 26, the capillary coil 31 and the evaporator coil 18, as shown in FIG. 3.

In this manner, the refrigerent circulating through the auxiliary condenser coil 32 is cooled by the fan 34 before being expanded to the lower pressure by the capillary coil 31 and returned to the evaporator coil 18.

As the liquid refrigerent passes through the evaporator coil 18 it is heated by the vapour driven off from the liquid in the compartment 15 whereby the refrigerent changes to the vapourous state and thereby absorbs heat from the vapour causing the vapour to condense.

The condensate is collected in the drip tray 16. The condensate is fed to the compartment 14 via the conduit 17. As the compartment 14 fills with condensate, the condensate can be drawn off via the tap in the compartment 14. If the tap is not operated, the condensate will fill the compartment 14 and subsequently spill over into the compartment 15, and will mix with the impure liquid in the compartment 15. If necessary, a further tap (not shown) may be provided in the lower portion of the compartment 14 to drain off contaminated liquid remaining in the compartment 15.

It will be appreciated that apparatus in accordance with the present invention is suitable for use in a chemical recovery plant.

It will also be appreciated that articles placed in tank 10 are cleaned by operation of the apparatus described above with reference to FIGS. 1 to 3 of the accompanying drawings and, in consequence, the apparatus the subject of the present invention may be used for cleaning articles.

We claim:

1. An apparatus for purifying liquid in a container comprising:

an enclosed container, said container having first and second adjacent compartments, said first compartment storing a liquid to be purified, said compartments vertically opening into a third compartment above said first and second compartments, said first, second and third compartment forming an enclosure;

a drip tray located within said container above said first and second compartments, said tray having a conduit for directing condensation incident thereto to said second compartment;

a refrigeration means having a coil disposed in said third compartment constituting an evaporator, and a second coil disposed in the bottom of said first compartment constituting a condenser, said refrigeration means further comprising a second condenser;

a capillary coil;

and a control means for selectively directing a refrigerant through a first circuit of elements and subsequently through a second circuit of elements, said first circuit comprising said condenser, second condenser, capillary coil and evaporator coil during the purification of a liquid in said first compartment, and said second circuit of elements comprising said first condenser, capillary coil, second condenser, and evaporator coil, whereby said control means provides for selectively changing the pressure of the refrigerant entering said evaporator.

2. Apparatus as claimed in claim 1 wherein the control means comprises slide valve means.

3. Apparatus as claimed in claim 1, wherein the refrigeration means includes a compressor and the second condenser is provided with means for agitating air adjacent said condenser, said agitating means being operable in response to temperature sensed in an upper portion of the compressor.

4. Apparatus as claimed in claim 3 wherein the agitating means comprises a fan and second control means for controlling the fan, the second control means being operable in response to temperature sensed in an upper portion of said compressor.

* * * * *